Feb. 15, 1944. R. L. BYRUM Plant Pat. 617
ROSE PLANT
Filed Oct. 15, 1943
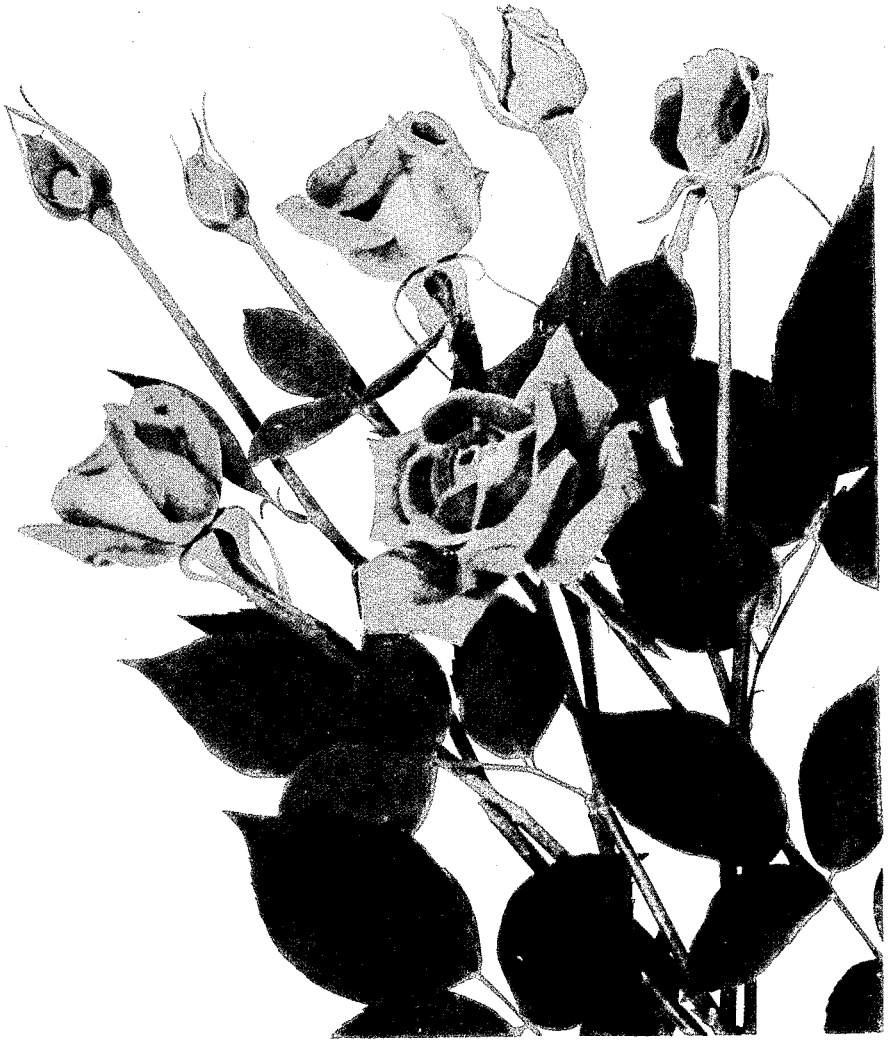
Inventor
Roy L. Byrum
By Robbs & Robbs
Attorneys Patented Feb. 15, 1944

Plant Pat. 617

UNITED STATES PATENT OFFICE

617

ROSE PLANT

Roy L. Byrum, Richmond, Ind., assignor to Joseph H. Hill Company, Richmond, Ind., a corporation of Indiana Application October 15, 1943, Serial No. 506,407

1 Claim. (Cl. 47—61)

The present invention relates to a new and distinct variety of rose plant, originated by the crossing of the two varieties "Better Times" (Pl. Pat. #23) and "Colleen Moore" (Pl. Pat. #582).

This new variety is distinguished from its parents primarily by the color of its flowers, being a bright velvety red color, and its fragrance, extra strong tea. It is sometimes similar, so far as the color of the flowers is concerned, to "Colleen Moore," though not as dark, as indicated above, but it is smaller in size than the latter.

In other respects, it differs in specific characteristics from the above varieties as more particularly pointed out in the following detailed description, all color terminology according with Ridgway's Color Standards, except where otherwise indicated, and asexual reproduction of the new rose shows that these characteristics come true to form:

Type: Half hardy; bush; greenhouse; seedling; for cut flowers.
Class: Hybrid tea.
Breeding: Seedling.
*Seed parent.*—"Better Times."
*Pollen parent.*—"Colleen Moore.'
Propagation: Holds its distinguishing characteristics through succeeding propagations by grafting and budding.

*Flower*

Locality where grown: Richmond, Indiana.
Flowers borne: Singly to stem, on normal, short stems.
Quantity of bloom: Abundant in greenhouse.
Continuity: Continuous.
Fragrance: Penetrating tea.
Bud:
*Peduncle.*—Short; medium heavy; erect; reddish bronze; smooth; few Yellow hairs.
*Before calyx breaks.—Size*—small. *Form*—short; pointed; ovoid, with a conspicuous neck; with foliaceous appendages on the surface of the bud; with slender foliaceous parts extending beyond the tip of the bud equal to one-half of its length.
*As calyx breaks.—Color*—Ox Blood Red, Plate 1, overlaid with Victoria Lake, Plate 1.
*As first petal opens.—Size*—small. *Form*—short; pointed; ovoid. *Color*—outside: Carmine, Plate 1, washed lightly with Victoria Lake, Plate 1; inside: Bright velvety red (no corresponding color value in Ridgway's Color Standards. *Opening*—opens up well.
Bloom:
*Size.*—When fully open, small; 2 to 3 inches.
*Petalage.*—Semi-double; from 25 to 30 petals arranged irregularly.
*Form.*—Open; full; globular at first, becoming open; petals remaining at first tightly rolled outward, becoming later, at maturity, very loosely rolled outward.
Petals: Thick; with inside velvety and outside shiny.
*Shape.*—Outside—obovate. Intermediate—obovate; scalloped with one notch. Inside—obovate; scalloped with one notch.

This description of a newly opened flower was made from a rose grown in a greenhouse during the month of February, 1943, at Richmond, Indiana:

*Color.—Outside petal*—outside surface: Rose Red, Plate XII, washed with Pomegranate Purple, Plate XII; inside surface: Carmine overlaid with deep velvety Red, Plate 1. *Intermediate petal*—outside surface: Rose Red, Plate XII, washed with Pomegranate Purple, Plate XII; inside surface: Carmine overlaid with deep velvety Red, Plate 1. *Inner petal*—outside surface: Rose Red, Plate XII, washed with Pomegranate Purple, Plate XII; inside surface: Carmine overlaid with deep velvety Red, Plate 1.

This description was made from a rose that was open for three days in a greenhouse during the month of September, 1943, at Richmond, Indiana:

*Color.—Outside petal*—outside surface: Tyrian Rose, Plate XII; inside surface: Tyrian Rose, Plate XII, washed with Pomegranate Purple, Plate XII. *Inside petal*—outside surface: Rose Color, Plate XII; inside surface: Tyrian Rose, Plate XII, penciled with Rose Red, Plate XII; (also Crimson Carmine, Plate #41, Koster's Color Guide).
*General color effect.*—Newly opened flower—Carmine overlaid with dark velvet, Plate 1. Three days open—Tyrian Rose, Plate XII, overlaid with Velvety Rose Red, Plate XII.
*Behavior.*—Persist.
*Flower longevity.*—As cut roses grown in greenhouse kept at living-room temperatures, 3 to 5 days in February.

*Reproductive organs*

Stamens: Medium number; arranged regularly about pistils.
Filaments: Medium long; reddish; most with anthers.
Anthers: Small; reddish; all open at once.
Pollen: Moderately abundant; Gold.
Pistils: Medium number.
Styles: Uneven; medium length; thin; bunched.
Stigma: White.
Ovaries: All enclosed in calyx.
Sepals: Permanent; long; spear-shaped; curled.
*Color.*—Chromium Green, Plate XXXII, inside. Chromium Green, Plate XXXII, outside.

*Plant*

Foliage:
*Leaves.*—Compound of five leaflets; very abundant; medium large; moderately heavy; leathery.
*Leaflets.*—*Shape*—ovoid with apex obtuse; base round; margin simply serrate.
*Color.*—*Mature*—upper surface: very Dark Green; under surface: moderately Light Green.
*Rachis.*—Medium heavy. Upper side—smooth; grooved; under side—extremely smooth.
*Stipules.*—Very short; very narrow; with moderately short points, turning out at an angle of less than 45°.
*Disease.*—Resistant to mildew and blackspot insofar as this is evidenced by absence of any throughout development and establishing of this variety.

Growth:
*Habit.*—Bush; upright; much branched.
*Growth.*—Vigorous.
*Canes.*—Moderately heavy.
*Main stems.*—Bright Green. *Thorns*—few; short; hooked downward; with short, round base. *Prickles*—none.
*Branches.*—Bright Green. *Thorns*—few; short; hooked downward; with short, round base. *Prickles*—none. *Hairs*—none.
*New shoots.*—Bright Bronze Red. *Thorns*—few; short; hooked downward; with short, round base. *Prickles*—none. *Hairs*—none.

I claim:

A new and distinct variety of rose plant, characterized as to novelty by the color, size, and fragrance of its flowers, substantially as shown and described.

ROY L. BYRUM.